(12) United States Patent
Gilet et al.

(10) Patent No.: US 9,062,293 B2
(45) Date of Patent: Jun. 23, 2015

(54) **BACTERIAL COMPOSITIONS OF *STAPHYLOCOCCUS VITULINUS* HAVING NITRATE REDUCTASE ACTIVITY AND OF LACTIC ACID BACTERIA AND METHODS USING THESE COMPOSITIONS**

(75) Inventors: Lionel Gilet, Brehand (FR); Caroline de Lamarliere, Tours (FR); Martine Perrin, Descartes (FR); Pascal Fourcassie, Poitiers (FR)

(73) Assignee: DANISCO A/S, Copenhagen K (DK)

( * ) Notice: Subject to any disclaimer, the term of this patent is extended or adjusted under 35 U.S.C. 154(b) by 572 days.

(21) Appl. No.: 13/139,081

(22) PCT Filed: Dec. 11, 2008

(86) PCT No.: PCT/IB2008/055672
§ 371 (c)(1),
(2), (4) Date: Aug. 25, 2011

(87) PCT Pub. No.: WO2010/067148
PCT Pub. Date: Jun. 17, 2010

(65) Prior Publication Data
US 2011/0300591 A1    Dec. 8, 2011

(51) Int. Cl.
| | |
|---|---|
| C12P 39/00 | (2006.01) |
| C12N 1/20 | (2006.01) |
| A23B 4/22 | (2006.01) |
| A23L 1/314 | (2006.01) |
| A23L 1/317 | (2006.01) |
| A23L 1/318 | (2006.01) |
| C12R 1/44 | (2006.01) |

(52) U.S. Cl.
CPC ... *C12N 1/20* (2013.01); *A23B 4/22* (2013.01); *A23L 1/31472* (2013.01); *A23L 1/317* (2013.01); *A23L 1/3185* (2013.01); *C12P 39/00* (2013.01); *C12R 1/44* (2013.01)

(58) Field of Classification Search
None
See application file for complete search history.

(56) References Cited

U.S. PATENT DOCUMENTS 6,063,410 A * 5/2000 Vedamuthu et al. ............ 426/56

FOREIGN PATENT DOCUMENTS

| EP | 1817962 | 8/2007 |
|---|---|---|
| WO | 2007/025097 | * 3/2007 |

OTHER PUBLICATIONS

H.Geneçcelep et al. "Effects of starter cultures and nitrite levels on formation of biogenic amines in sucuk", Meat Science 77:424-430. (Apr. 2007).*
Drosinos et al., "Phenotypic and technological diversity of lactic acid bacteria and *Staphylococci* isolated from traditionally fermented sausages in Southern Greece," Food Microbiol., 24(3):260-270 (2006) XP005807866.
International Search Report and Written Opinion in PCT/IB2008/055672, dated Oct. 19, 2009.
Kramer et al., "Lebensmittel-Mikrobiologie," Eugen Ulmer, pp. 296-309 (1997) XP002547379.
Sanz et al., "Effect of pre-ripening on microbial and chemical changes in dry fermented sausages," Food Microbiology, 14(6):575-582 (1997) XP002479818.
Villani et al., "Microbial ecology of the soppressata of Vallo di Diano, a traditional dry fermented sausage from southern Italy, and in vitro and in situ selection of autochthonous starter cultures," Appl. Environ. Microbiol., 73(17):5453-5463 (2007) XP002479817.

* cited by examiner

*Primary Examiner* — Rebecca Prouty
(74) *Attorney, Agent, or Firm* — McAndrews, Held & Malloy Ltd.

(57) ABSTRACT

The invention relates to a method for converting nitrates to nitrites and to specific compositions of bacteria belonging to the *Staphylococcus vitulinus* species optionally in association with lactic acid bacteria such as *Lactococcus* genus or *Pediococcus* genus and their use for developing the red color of a food product containing myoglobin.

19 Claims, No Drawings

“Bacterial starter cultures for meat fermentation”, published in Food Chemistry, Volume 59, 4, pages 547-557, 1997, it is mentioned that, in the fermented sausage industry, the use of ferments consisting of a mixture of lactic acid bacteria strains with bacteria having nitrate reductase activity, is well established. Such bacterial mixtures are also disclosed in a book by J. Bacus, entitled "Utilization of microorganisms in meat processing, a handbook for meat plant operators", published in 1984 by the publisher Research Studies Press Ltd.

BACTERIAL COMPOSITIONS OF STAPHYLOCOCCUS VITULINUS HAVING NITRATE REDUCTASE ACTIVITY AND OF LACTIC ACID BACTERIA AND METHODS USING THESE COMPOSITIONS

The present application is filed pursuant to 35 U.S.C. 371 as a U.S. National Phase application of International Patent Application No. PCT/IB2008/055672, which was filed Dec. 11, 2008. The entire text of the aforementioned application is incorporated herein by reference in its entirety.

FIELD OF THE INVENTION

The present invention relates to a method for converting nitrates to nitrites and to specific compositions of bacteria and their use for developing the red color of a food product containing myoglobin.

BACKGROUND OF THE INVENTION

Lactic bacteria are commonly used as ferments during the manufacture of certain food products, such as milk-based products (yogurts, cheeses, etc.), bakery products, wine, and meat-based products. In particular, these bacteria are used for their acidifying capacity. Indeed, lactic acid bacteria are capable of converting sugars (glucose, lactose, etc.) into lactic acid, or other acids, such as acetate, thereby provoking a decrease in pH.

Other types of bacteria are also commonly used as ferments; in particular bacteria which display nitrate reductase activity (NRA), such as certain bacteria of the *Staphylococcus* genus. These bacteria play an important role in the agri-food industry. In addition to their possible use for flavouring foods, these bacteria can be involved during nitrate-to-nitrite conversion processes, and more widely during a process for the manufacture of food products that includes such a step. Indeed, bacteria having NRA can be involved in the coloration of food products comprising myoglobin, irrespective of whether said products undergo a cooking step.

Thanks to the use of bacteria having NRA, in combination with nitrates that they will convert into nitrites (in situ nitrite production), it is possible to reduce the amount of nitrites used for the manufacture of food products such as cured products, or even to eliminate the introduction of chemical nitrites. Indeed, it is desirable to limit the amount of added nitrites since they can react with other compounds to form nitrosamines, which are known to be carcinogenic.

Bacterial combinations comprising lactic acid bacteria together with bacteria having NRA have also been developed and used as ferments during the manufacture of food products.

In the publication by M. Hugas and J. M. Monfort, entitled However, such combinations are not always advantageous. For example, a publication by L H Stanke, entitled "Dried sausages fermented with *Staphylococcus xylosus* at different temperatures and with different ingredient levels", published in 1995 in Meat Science, volume 41, No. 2, pages 179-191, discloses sausages incorporating *Staphylococcus xylosus* with various elements including the acidifying bacterium *Pediococcus pentosaceus*. Various temperatures are tested. The study reveals that the best temperature is 30° C. and the use of the lactic acid bacterium with *Staphylococcus xylosus* is not recommended, since the lactic acid bacteria appear to play an inhibitory role.

In the existing prior art combining both *Staphylococcus* and lactic acid bacteria, the lactic acid bacteria are used for their acidifying capacity and *Staphylococcus* strains are used for their NRA.

SUMMARY OF THE INVENTION

In the present invention, the inventors disclose a surprising synergy: lactic acid bacteria, or even a medium having been in contact with lactic acid bacteria, can increase the nitrate reductase activity (NRA) of bacteria belonging to the *Staphylococcus vitulinus* specie. This effect presents great advantages for the agri-food industry. First, it improves the yield of nitrate-to-nitrite conversion processes. Then, it accelerates the development of the red color of a food product containing myoglobin.

The present invention therefore relates to a method for converting nitrates to nitrites, wherein nitrates are converted to nitrites by bacteria belonging to the *Staphylococcus vitulinus* specie having nitrate reductase activity (NRA), in the presence of lactic acid bacteria, at a pH comprised between 5.2 and 9.

The present invention therefore relates to a method for converting nitrates to nitrites, wherein nitrates are converted to nitrites by bacteria belonging to the *Staphylococcus vitulinus* specie having nitrate reductase activity (NRA), in the presence of a medium which has been in contact with lactic acid bacteria and is substantially free of bacteria, at a pH comprised between 5.2 and 9.

DETAILED DESCRIPTION OF THE INVENTION

The present invention therefore relates to a method for converting nitrates to nitrites, wherein nitrates are converted to nitrites by bacteria belonging to the *Staphylococcus vitulinus* specie having nitrate reductase activity (NRA), in the presence of lactic acid bacteria, at a pH comprised between 5.2 and 9.

The invention also relates to the use of bacteria belonging to the *Staphylococcus vitulinus* specie having nitrate reductase activity (NRA) for converting nitrates to nitrites in the presence of lactic acid bacteria, at a pH comprised between 5.2 and 9.

The present invention therefore relates to a method for converting nitrates to nitrites, wherein nitrates are converted to nitrites by bacteria belonging to the *Staphylococcus vitulinus* specie having nitrate reductase activity (NRA), in the presence of a medium which has been in contact with lactic acid bacteria and is substantially free of bacteria, at a pH comprised between 5.2 and 9.

The invention also relates to the use of bacteria belonging to the *Staphylococcus vitulinus* specie having nitrate reductase activity (NRA) for converting nitrates to nitrites in the presence of a medium which has been in contact with lactic acid bacteria and is substantially free of bacteria, at a pH comprised between 5.2 and 9.

Another object of the invention is the use of lactic acid bacteria, or of a medium which has been in contact with lactic acid bacteria and is substantially free of bacteria, for increasing the nitrate reductase activity (NRA) of bacteria belonging to the *Staphylococcus vitulinus* specie, in the presence of nitrates, at a pH comprised between 5.2 and 9.

As used herein, the term "bacteria" is intended to mean one or several bacteria, i.e. it can refer both to one or several cells of a given bacterial strain and to bacteria from several bacterial strains.

The term "bacteria having nitrate reductase activity (NRA)" as used herein refers to bacteria which are capable of converting nitrates to nitrites.

NRA can be measured according to test A, which is carried out as follows.

Test A, carried out at a given temperature T, comprises the following three steps:

Step 1: 10 g of the bacterium to be tested, in freeze-dried form, are hydrated in 90 g of tryptone salt liquid medium which comprises 0.9% by weight of NaCl and 1% by weight of tryptone casein, at room temperature for 10 minutes, with shaking at 200 rpm.

Step 2: a volume of 1 ml of the mixture obtained in step 1 is diluted in 50 ml of a reaction medium comprising:
45 ml of phosphate buffer at a pH of 6.9 at a concentration of 0.1M;
between 0.5 g and 3 g of NaCl;
between 0.5 g and 1.5 g of glucose, sucrose and/or lactose;
0.15 g of $KNO_3$ or $NaNO_3$;
and tryptone salt qsp 50 ml.

The whole mixture is then incubated for a period t (expressed in hours or minutes) at temperature T (t depends on the given temperature T).

Step 3: the nitrites produced are assayed by the Griess-LLosvays reagent method (according to "Bacterial nitrate reductases: Molecular and biological aspects of nitrate reduction", P. J. Gonzalez et al., 2006, J. of Inorganic Biochemistry, 100, 1015-1023) and the reaction rate is calculated.

The reaction rate is evaluated by measuring at the end point the amount of nitrite $NO_2^-$ produced. The reaction is estimated to be equimolar between the nitrate $NO_3^-$ converted and the nitrite $NO_2^-$ produced.

It is expressed in μg of $NO_3^-$ converted per minute and per $10^{11}$ cfu (which stands for "colony forming unit"). It corresponds to the initial speed of conversion of nitrates to nitrites. The skilled person will determine the values of the period t depending on the values of the temperature T he chooses.

The period t will be of 16 hours when T is lower than 20° C. (for example 4° C. or 11° C.) The period t will be of 1 hour and a half when T is 25° C. The period t will be of 30 minutes when T is 44° C.

Advantageously, the synergistic effect discovered by the inventors is observed over a wide range of temperatures, including, surprisingly, at low temperatures. The temperature can be lower than 16° C. Surprisingly, the synergistic effect can also be observed when the temperature is comprised between 4° C. and 11° C.

Preferably, the conversion of nitrates to nitrites by the bacteria belonging to the *Staphylococcus vitulinus* specie and having NRA in the presence of lactic bacteria (respectively, a medium having been in contact with a lactic bacteria and substantially free of bacteria) is carried out at low temperature, such as 16° C., 11° C. or even 4° C.

By "low temperature" it is intended a temperature inferior or equal to room temperature, preferably inferior or equal to 25° C., preferably inferior or equal to 20° C., even more preferably inferior or equal to 16° C., to 14° C., to 11° C., to 8° C. or 4° C.

Accordingly, in one embodiment, the bacteria having NRA and belonging to the *Staphylococcus vitulinus* specie has significant NRA at low temperature.

The expression "bacteria having significant NRA at low temperature" means a bacterium which has a NRA of greater than or equal to 50 μg of $NO_3^-$ converted per minute and per $10^{11}$ cfu according to test A performed at T=11° C.

Advantageously, the bacteria having NRA and belonging to the *Staphylococcus vitulinus* specie may display a NRA of greater than or equal to 56 μg of $NO_3^-$ converted per minute and per $10^{11}$ cfu, preferably greater than or equal to 70 μg of $NO_3^-$ converted per minute and per $10^{11}$ cfu, or even more preferably greater than or equal to 80 μg of $NO_3^-$ converted per minute and per $10^{11}$ cfu, according to the test A performed at T=11° C.

Advantageously, the bacteria belonging to the *Staphylococcus vitulinus* specie may display a NRA of greater than or equal to 4 μg of $NO_3^-$ converted per minute and per $10^{11}$ cfu according to the test A performed at T=4° C.

Preferably, the bacteria belonging to the *Staphylococcus vitulinus* specie may display a NRA of greater than or equal to 15 μg of $NO_3^-$ converted per minute and per $10^{11}$ cfu, even more preferably greater than or equal to 25 μg of $NO_3^-$ converted per minute and per $10^{11}$ cfu according to the test A performed at T=4° C.

This presents an advantage over the methods for converting nitrates to nitrites disclosed in the prior art, wherein the nitrate-to-nitrite reduction is generally performed at room temperature or higher temperatures. Indeed, the NRA of bacteria having such activity is generally observed at temperatures comprised between 35° C. and 48° C. in the prior art. However, manufacturing methods which require nitrate-to-nitrite conversion at high temperatures are more costly and more difficult to implement than methods which can be carried out at room temperature.

Moreover, the use of room temperatures or higher during processes for manufacturing food products can prove to be unsuitable since such temperatures can promote the development of certain pathogenic bacteria (such as *Listeria monocytogenes, Escherichia coli* 0157: H7, *Salmonella typhimurium, Campylobacter jejunii*).

The bacteria belonging to the *Staphylococcus vitulinus* specie and having nitrate reductase activity may be in an industrial stabilization form, according to the techniques known to those skilled in the art. Indeed, the bacteria may be in a dried form (dried by atomization, freeze-drying, heating, etc.), in a frozen form, in a concentrated liquid form, etc. In a preferred embodiment, the bacteria belonging to the *Staphylococcus vitulinus* specie is in a freeze-dried form. When this is not the case, the determination of its NRA according to the test A will be possible via a pre-step consisting in converting it into a freeze-dried form, according to conventional techniques known to those skilled in the art.

In a preferred embodiment, the bacteria belonging to the *Staphylococcus vitulinus* specie and having nitrate reductase activity are the *Staphylococcus vitulinus* strain deposited under the Budapest Treaty at the COLLECTION NATIONALE DE CULTURES DE MICROORGANISMES (CNCM) [National Collection of Microorganism Cultures, Institut Pasteur, 25, rue du Docteur Roux, F-75724 Paris Cedex 15, France] by Danisco France SAS, 20 rue de Brunel, 75017 Paris on 25 Apr. 2007 and bearing the number CNCM I-3751.

The method according to the invention may use, in addition to *Staphylococcus vitulinus*, other bacteria having nitrate reductase activity, such as for example *Staphylococcus carnosus* and/or *Staphylococcus xylosus*.

In one embodiment, the method may use bacteria having NRA and belonging to the specie *Staphylococcus vitulinus* with the *Staphylococcus carnosus* strain deposited at the CNCM under the Budapest Treaty by Danisco France SAS on 12 Oct. 2007 and bearing the number CNCM I-3844 and/or the *Staphylococcus xylosus* strain deposited with the CNCM under the Budapest Treaty by Danisco France SAS on 12 Oct. 2007, and bearing the number CNCM I-3845.

In a specific embodiment, the *Staphylococcus vitulinus* strain CNCM I-3751 and the *Staphylococcus carnosus* strain CNCM I-3844 are mixed.

In another specific embodiment, the *Staphylococcus vitulinus* strain CNCM I-3751 and the *Staphylococcus xylosus* strain CNCM I-3845 are mixed. In another embodiment, the *Staphylococcus vitulinus* strain CNCM I-3751, the *Staphylococcus carnosus* strain CNCM I-3844 and the *Staphylococcus xylosus* strain CNCM I-3845 are mixed.

The nitrates useful for the methods according to the invention may be of natural or chemical origin.

The nitrates may be of chemical origin. They may, for example, be potassium nitrate, sodium nitrate, saltpeter, and mixtures thereof.

However, the nitrates are preferably of natural origin. They are preferably provided by at least one plant and/or one extract of at least one plant. The plant is advantageously chosen from plants naturally rich in nitrates. Mention may, for example, be made of leek, celery, onion, spinach, cabbage, etc.

The nitrates may be provided in liquid and/or solid form.

The nitrates may be contained in a liquid preparation, in which they have been recovered, into which they have been introduced and/or in which they have been concentrated, in particular after extraction from a natural source of nitrates. It may, for example, be a broth of at least one plant naturally rich in nitrates.

In a specific embodiment, the liquid preparation of nitrates is a liquid buffer preparation, i.e. a neutral medium containing nitrates which have been recovered, introduced and/or concentrated, in particular after extraction from a natural source of nitrates, such as, for example, from at least one plant naturally rich in nitrates.

The nitrates may also be provided in a solid form, in particular from at least one plant or a part of a plant naturally rich in nitrates. It may, for example, be a leek or spinach leaf, a fragment of celery, of onion or of cabbage, etc.

The nitrites derived from the conversion may, for example, play a role as preserving agents.

The conversion of nitrates to nitrites by bacteria belonging to the *Staphylococcus vitulinus* specie and having NRA in the presence of lactic acid bacteria (respectively, in the presence of a medium having been in contact with a lactic acid bacteria and substantially free of bacteria) is carried out at a pH comprised between 5.2 and 9, preferably at a pH comprised between 5.4 and 8, so that the conversion occurs. Typically, the pH is superior or equal to 5.2, preferably superior or equal to 5.4, even more preferably superior or equal to 5.6.

Typically, the pH according to the invention is inferior or equal to 9, preferably inferior or equal to 8, preferably inferior or equal to 7.8, even more preferably inferior or equal to 7.4.

In a preferred embodiment, the pH is about 6.9. To maintain the pH to a value between 5.2 and 9 (or to any preferred value above mentioned), a buffer medium can be used. The buffer medium may be, for example, a phosphate buffer.

The term "lactic acid bacteria" has its general meaning in the art. It refers to bacteria which are capable of converting sugars (glucose, lactose, etc.) into lactic acid, or other acids, such as acetate, thereby provoking a decrease in pH, unless said pH is buffered by other means.

According to one embodiment of the invention, the conversion of nitrates to nitrites is carried out in the presence of lactic acid bacteria. The fermentation and/or culture medium of said lactic acid bacteria can also be present.

The lactic acid bacteria can be used with their fermentation and/or culture medium. The medium may be liquid or solid. The bacteria and the metabolites produced by these bacteria during the fermentation and/or the culture are present or dispersed in the fermentation and/or culture medium in which they were initially placed.

The lactic acid bacteria may be live bacteria. They may also have been inactivated after fermentation and/or culture, by heat treatment, by chemical treatment and/or by mechanical treatment, such as the treatments known to and used by those skilled in the art. Such treatments may or may not induce degradation of the lactic acid bacteria.

These bacteria may also have been concentrated, i.e., after culture and/or fermentation in an appropriate medium, they have been recovered in a "biomass harvest" step, according to the techniques known to those skilled in the art (after centrifugation, filtration, distillation, etc.). They may then be in a concentrated liquid form.

In one variant of the invention, these bacteria may be in an industrial stabilization form, i.e. they have undergone a conservation step (irrespective of whether or not they are concentrated) according to the techniques known to those skilled in the art. They may be in a dried form, i.e. they have undergone a drying step (by atomization, freeze-drying, heating, etc.). The lactic acid bacteria may also be in a frozen form. In a preferred embodiment, the lactic acid bacteria are advantageously in freeze-dried form.

When the lactic acid bacteria are concentrated and/or stabilized, part of the fermentation and/or culture medium, with the bacteria and their metabolites produced during the fermentation and/or the culture, still remains.

The ratio of the amount of bacteria having NRA and belonging to the specie *Staphylococcus vitulinus*, and the amount of lactic acid bacteria for the method according to the invention may be between 1:100 and 1:0.01, preferably between 1:10 and 1:0.1. It may be between 1:5 and 1:0.5, or else between 1:1 and 1:0.7.

The conversion of nitrates-to-nitrites according to the invention may be carried out in a solution comprising between $10^9$/g and $8 \times 10^{12}$/g cfu bacteria belonging to the *Staphylococcus vitulinus* specie and between $10^9$/g and $10^{12}$/g cfu of lactic acid bacteria.

In a preferred embodiment, the lactic acid bacteria are selected from the group consisting of bacteria of the Lactococcus genus, bacteria of the *Pediococcus* genus, and mixtures thereof. They may for instance be selected from the group consisting of species *Lactococcus Lactis, Pediococcus acidilactici* and *Pediococcus pentasaceus*, alone or in combination.

Other lactic acid bacteria may be combined with *Pediococcus* and/or *Lactococcus* in order to form the bacterial preparation. They may be *Streptococcus, Leuconostoc, Oenococcus, Vagococcus, Bifidobacterium*, etc.

In one embodiment, the lactic acid bacteria do not belong to the subspecies *Streptococcus lactis* subsp. *diacetylactis*, also known as *Lactococcus lactis* subsp *diacetylactis*.

In a preferred embodiment, the lactic acid bacteria belong to the specie *Pediococcus acidilactici*.

In a preferred embodiment, the lactic acid bacteria are the *Pediococcus acidilactici* strain deposited with the CNCM under the Budapest Treaty by Danisco France SAS, 20 rue Brunel 75017 PARIS, on 9 Dec. 2008, and bearing the number CNCM I-4098.

In a preferred embodiment, the lactic acid bacteria display a low acidifying capacity at low temperature.

In order to measure the acidifying capacity of a bacterium, the test B may be used, and the CINAC (acidification kinetics) software may, for example, be used. The test B is the following:

1) Preparation of a medium based on meat extract The following ingredients are mixed in a beaker: 200 g of powdered meat extract (extract used for the preparation of culture media for bacteriological control, and that can be purchased from the companies Difco LTD, Organo Technie, Solabia, etc.), 6 g of anhydrous glucose, 10.52 a of lactose monohydrate. 4 or 5 drops of an antifoam and approximately 700 ml of distilled water are added. The whole is ground and then the volume is made up to 1000 ml with distilled water.

2) Inoculation of the lactic acid bacterium and incubation

When the lactic acid bacterium is present in a freeze-dried form, 5 g are hydrated in 45 g of Tryptone salt liquid medium which comprises 0.9% by weight of NaCl and 1% by weight of Tryptone casein, at ambient temperature for 15 minutes, with stirring at 200 rpm.

The level of inoculation of the medium based on meat extract is adjusted to as to obtain an initial concentration of lactic acid bacteria of $6 \times 10^6$ cfu/ml of medium based on meat extract.

The acidifying activity is reflected by continuously recording the pH for a certain period, at a given incubation temperature.

The expression "lactic acid bacterium having a low acidifying capacity at low temperature" is intended to mean a lactic acid bacterium which has an acidifying capacity of less than 0.25 U pH (pH unit) after 4 days of incubation at 11° C. The lactic acid bacterium may also display an acidifying capacity of less than 0.20 U pH after 4 days of incubation at 11° C., preferably an acidifying capacity of less than 0.15 U pH after 4 days of incubation at 11° C.

It may also have an acidifying capacity of less than 0.1 U pH after 4 days of incubation when the temperature is equal to 4° C., preferably of less than 0.1 U pH after 6 days of incubation when the temperature is equal to 4° C., preferably of less than 0.1 U pH after 8 days of incubation when the temperature is equal to 4° C., more preferably of less than 0.1 U pH after 10 days of incubation when the temperature is equal to 4° C.

According to another embodiment of the invention, the composition used for converting nitrates to nitrites comprises a medium which has been in contact with lactic acid bacteria and is substantially free of bacteria, instead of lactic acid bacteria themselves (wherein their fermentation and/or culture medium can also be present). Preferred lactic acid bacteria useful for preparing said medium are as defined above for the embodiments using lactic acid bacteria themselves.

In a preferred embodiment, the medium which has been in contact with lactic acid bacteria and which is substantially free of bacteria is a liquid medium. The medium which has been in contact with lactic acid bacteria and which is substantially free of bacteria can also be a powder medium or a dried medium. Such a medium could be obtained from a liquid medium after a drying step for example. It could eventually be subsequently rehydrated to provide again a liquid medium.

The term "substantially free of bacteria", when applied to a liquid medium, refers to either a liquid medium which contains no more than 100 cfu/ml, preferably no more than 50 cfu/ml, preferably no more than 10 cfu/ml preferably no more than 1 cfu/ml, preferably no more than cfu/10ml. Alternatively, when applied to a powder or dried medium, it refers to a medium which contains no more than 100 cfu/mg, preferably no more than 50 cfu/mg, preferably no more than 10 cfu/mg, preferably no more than 1 cfu/mg, even more preferably no more than 1 cfu/10 mg.

The term "medium" is intended to mean culture medium and/or fermentation medium.

The term "culture medium" is intended to mean a medium which allows the development of the biomass. It contains a source of carbohydrates, a source of nitrogen, a source of phosphorus, a source of vitamins and a source of minerals.

The term "fermentation medium" is intended to mean a fermentation medium which allows the production of bacterial metabolites and/or the growth of the biomass. It contains a source of carbohydrates and/or a source of nitrogen and/or a source of phosphorus, and a source of vitamins and a source of minerals.

A given medium may be both a culture and fermentation medium.

The composition of the fermentation and/or culture medium and also the conditions for carrying out the fermentation/culture may be the following:

Amount of lactic acid bacteria added to a fermentation and/or culture medium:

Between $10^6$ cfu/ml and $10^{12}$ cfu/ml when the culture medium is liquid.

Between $10^8$ and $10^{14}$ cfu/cm$^2$ when the culture medium is solid.

Composition of the fermentation and/or culture medium in the liquid state:

The fermentation and/or culture medium comprises at least:

Between 1 mg/l and 100 g/l of carbohydrates (polyols, polysaccaharides, pentoses, hexoses and derivatives, fatty acids, etc.);

Between 1 mg/l and 100 g/l of nitrogenous substances (peptones, yeast extract, hydrolyzed proteins, proteins, peptides, amino acids, nitrogeneous bases and derivatives, etc.);

Between 1 µg/l and 10 g/l of phosphorus-containing substance (diamonium phosphate, inorganic mineral phosphate, natural phosphate, etc.);

Between 1 µg/l and 10 g/l of minerals (Mn, Mg, Cu, Zn, Mo, Ca, Na, Cl, Fe, Co, S, K, Li, Se, Cr, Ni, Pt, Ag, Cd, Al, etc.);

Between 1 µg/l and 1 g/l of vitamins (B12, biotin, nicotinamide, pantothenic acid, group B vitamins, group D vitamins, vitamin E, vitamin A, etc.).

Composition of the fermentation and/or culture medium in the solid state:

The fermentation and/or culture medium comprises at least the elements present in the medium in the liquid state, to which is added a gelling agent, the amount of which depends on the desired gelling strength (between 1% and 15% (w/w) of gelling agent). It may be agar, agarose, gums, alginates, etc.

Operating conditions:

The fermentation time ranges between 2 h and 5 days. The fermentation is carried out at a temperature of between 4° C. and 45° C.

The pH is comprised between 1.5 and 9.5.

When the fermentation medium is liquid, it is possible to agitate it by methods known to those skilled in the art (use of paddles, a vortex, by bubbling, etc.).

Since lactic acid bacteria are facultative and anaerobic bacteria, they can preferentially be used under anaerobic conditions or under microanaerobic or aerobic conditions.

The liquid medium may be, for example, a supernatant, a filtrate or a distillate that can be obtained:

α) from a fermentation and/or culture medium in which the lactic acid bacteria were initially placed, β) or after having returned to solution the lactic acid bacteria which may or may not have been concentrated, as they were described above, whether or not they have undergone a stabilization process.

In this case, contains only the substances secreted by the lactic acid bacteria during the fermentation and/or the culture, and elements of the solid or liquid fermentation medium, and is substantially free of bacteria.

In case α), after a fermentation time of at least 2 h at a temperature of between 4° C. and 65° C., the lactic acid bacteria are physically removed.

When the fermentation medium is a solid-state medium, the lactic acid bacteria may be scraped from the surface of the medium using any type of suitable spatula.

When the fermentation medium is a liquid-state medium, the lactic acid bacteria may be removed by methods known to those skilled in the art, such as centrifugation, filtration, distillation, etc. It is possible to use these methods alone or in combination.

The supernatant is the liquid medium from which the bacteria have been removed by centrifugation. A centrifuge with a gravitational force of between 400 and 65 000 g, preferably between 4000 and 10 000 g, may be used for example.

The filtrate, also called "culture liquor", is the liquid recovered after the liquid medium has been filtered through a filter of suitable porosity.

The distillate is the liquid obtained after the culture and/or fermentation medium has been boiled and then the vapor obtained (comprising in particular water and volatile compounds) has been condensed by means of a condenser.

It is also possible to obtain a liquid medium that is substantially free of bacteria and that has been in contact with lactic acid bacteria, after having returned to solution the lactic acid bacteria: this is case β). These bacteria may or may not have been concentrated, as they were described above, and they have or have not undergone a stabilization process. As described above, after having cultured and/or fermented the lactic acid bacteria in their fermentation and/or culture medium, said bacteria may have been concentrated. It is therefore possible to return them to solution according to techniques known to those skilled in the art (dilution, etc.), in order to in some way recreate a new fermentation and/or culture medium in which the lactic acid bacteria are finally dispersed. Then, in the same manner as in case α), a supernatant, a filtrate or a distillate can then be obtained.

Still in case β), the liquid medium may also be obtained from bacteria that have undergone a conservation step (whether or not they are concentrated). In fact, it is also possible to return conserved bacteria to solution by techniques known to those skilled in the art (by thawing when the bacteria have been frozen, by rehydration when they have been dried, etc.).

In a specific example, it is possible to obtain a liquid medium, and in particular a supernatant, a filtrate or a distillate, from freeze-dried bacteria. They may, for example, be rehydrated in a suitable medium, such as, for example, tryptone salt liquid medium comprising 0.9% by weight of NaCl, 1% by weight of tryptone casein, and then methods known to those skilled in the art can be applied, such as centrifugation, filtration, distillation, etc., which methods may be cumulative, in order to obtain a supernatant, a filtrate or a distillate.

In particular, the method disclosed in Example 2)b) may be used for obtaining a liquid medium which has been in contact with lactic bacteria but is substantially free of bacteria.

As already mentioned, the medium used in the present invention can also be a powder medium or a dried medium that could be obtained from any liquid medium above mentioned above (for instance, obtained after a drying step).

In one embodiment of the invention, the lactic acid bacteria (respectively the medium which has been in contact with lactic acid bacteria and is substantially free of bacteria) can be present together with the bacteria belonging to *Staphylococcus vitulinus* specie having NRA in the form of a composition.

In another embodiment, the method comprises the step of adding the lactic acid bacteria (respectively the medium which has been in contact with lactic acid bacteria and is substantially free of bacteria) to the bacteria belonging to *Staphylococcus vitulinus* specie having NRA, prior to the conversion of nitrates-to-nitrites step, which is carried out at a pH between 5.2 and 9.

In one embodiment of the invention, nitrates are added to the bacteria belonging to *Staphylococcus vitulinus* specie having NRA (the lactic acid bacteria or the medium which has been in contact with lactic acid bacteria and is substantially free of bacteria being already present or not) before the pH is regulated to a value comprised between 5.2 and 9.

In another embodiment of the invention, nitrates are added to the bacteria belonging to *Staphylococcus vitulinus* specie having NRA (the lactic acid bacteria or the medium which has been in contact with lactic acid bacteria and is substantially free of bacteria being already present or not) at a pH already comprised between 5.2 and 9.

According to the invention, conversion of nitrates to nitrites takes place at least when the bacteria belonging to *Staphylococcus vitulinus* specie having NRA are in the presence of the lactic acid bacteria or the medium which has been in contact with lactic acid bacteria and is substantially free of bacteria, nitrates, and at a pH comprised between 5.2 and 9.

The invention also relates to a method for developing the red color and/or increasing the stability and/or the intensity of the red color of a food product containing myoglobin, wherein said method comprises the conversion of nitrates to nitrites as described above.

Indeed, the conversion of nitrates to nitrites will be more rapid using the method of the present invention. The nitrites obtained are converted to nitric oxides which will be able to react with the myoglobin contained in the food product and give red color to the product. If the process for the manufacture of the food product comprises a heating step (after the nitrate-to-nitrite conversion step), the color development is further promoted. If the process for the manufacture of the food product comprises a cooking step (after the nitrate-to-nitrite conversion step), the color development is further promoted and the color obtained is more stable, due to the denaturation of the nitrosomyoglobin (NO+myoglobin).

The food product containing myoglobin may be chosen from products of animal origin. It may in particular be any meat-based product. Said meat may or may not be minced, with or without nitrates, with or without nitrites. Mention may be made of products based on bovine meat (bullock, cow, calf), on pork meat, on poultry meat (turkey hen, turkey cock, hen, chicken, female duck, male duck, etc.), on game meat (wild boar, the *Cervidae*, etc.) or on any other category of meat (mutton, lamb meat, rabbit meat, horse meat, ostrich meat, kangaroo meat, etc.).

It may also be any product based on fish, whether they are freshwater fish or saltwater fish (seas, oceans, etc.), and/or based on crustaceans. Mention may, for example, be made of products based on salmon, trout, tuna, shark, cod, crab, shrimp, Mediterranean prawns, langoustine, etc.

According another object of the invention is a method for the manufacture of a food product, comprising the conversion of nitrates-to-nitrites according to the method described above.

The food product may be an animal food product as described above containing myoglobin, as described above. It may also be any milk-based product, such as cheeses, preferably matures cheeses.

It may also be a food product of plant origin, such as a product based on fermented plant products, such as miso. It may also be based on fermented soybeans, for example tofu.

The food product may be mixtures of the products listed above.

In a preferred embodiment, the invention relates to a method for manufacturing a meat product.

In a preferred embodiment, the invention relates to a method for manufacturing a cured product, such as sausages, sausage meats, hams, etc.

In another preferred embodiment, the invention relates to a method for manufacturing a cooked meat product such as a cooked ham.

In one embodiment, the invention relates to a method for manufacturing a cooked ham comprising the following steps:
 Step 0=pre-step (pre-conversion of nitrates to nitrites):
 Preparation of the Solution
 A source of nitrates (between 0.10%(w/w) and 0.20% (w/w) of the brine) is mixed with water (at a temperature of 15° C. and which represents between 9% (w/w) and 14% (w/w) of the brine), until a homogeneous mixture is obtained. The mixture of bacteria (between 0.01% (w/w) and 0.25% (w/w) of the brine) as described, and exemplified above, is added and the resulting mixture is mixed until a homogeneous mixture is obtained.

The mixture can be left to stand overnight, preferably at low temperature, i.e. at a temperature below 16° C., preferably of between 4° C. and 11° C.
 Step 1: Preparation of the Meat
 This is the trimming step, which consists in removing the fat and the connective tissues from a given amount of meat.
 Step 2: Grinding
 The meat is then ground as desired.
 Step 3: Preparation of the Brine
 A given amount of water (represents between 60% and 70% of the brine) is weighed out and salt (represents between 12% and 24% of the brine) is added. The whole is mixed until the salt has completely dissolved.

The solution obtained in step 0, containing the source of partially reduced nitrates and the bacteria, and also dextrose (represents between 3% and 9% of the brine) and sodium tripolyphosphate (represents between 0.15% and 0.7% of the brine), are added and the whole is mixed for 5 minutes. The temperature is generally between 4 and 11° C.
 Step 4: Injection
 A defined amount of brine is injected into the ground meat obtained in step 2.
 Step 5: Churning (Kneading)
 The whole is mixed for 4 hours at 8 rpm continuously (80% vacuum). The temperature is generally between 8 and 12° C.
 Step 6: Moulding and Shaping
 Step 7: Cooking
 The ham is cooked at a surrounding temperature of 78° C. until 72° C. is reached at the heart of the product.
 The product is then cooled by showering.

In another embodiment, the invention relates to a method for manufacturing a cooked ham, without a step of pre-conversion of nitrates to nitrites, comprising the following steps:
 Step 1: Preparation of the Meat
 This is the trimming step, which consists in removing the fat and the connective tissues from a given amount of meat.
 Step 2: Grinding
 The meat is then ground as desired.
 Step 3: Preparation of the Brine
 A given amount of water (represents between 60% and 70% of the brine) is weighed out and salt (represents between 12% and 24% of the brine) is added. The whole is mixed until the salt is completely dissolved.

The source of nitrates (represents between 0.10% and 0.20% of the brine) with the mixture of bacteria (represents between 0.01% and 0.25% of the brine), and also dextrose (represents between 3% and 9% of the brine) and sodium tripolyphosphate (represents between 0.15% and 0.7% of the brine), are added and the whole is mixed for 5 minutes. The temperature is generally between 4 and 11° C.
 Step 4: Injection
 A defined amount of brine is injected into the ground meat obtained in step 2.
 Step 5: Churning (kneading)
 The whole is mixed for 16 hours at 4 rpm batchwise (30 minutes standing and 30 minutes working) (80% vacuum). The temperature is generally between 8 and 12° C.
 Step 5': Leaving standing for 24 hours
 The temperature is generally below 16° C., preferably between 4° C. and 11° C.
 Step 6: Moulding and Shaping
 Step 7: Cooking
 The ham is cooked at a surrounding temperature of 73° C. until 70° C. is reached at the heart of the product. The product is then cooled by showering.

Another aspect of the invention concerns compositions suitable for carrying out the method as described above.

The invention relates to a composition comprising:
 a) bacteria belonging to the *Staphylococcus vitulinus* specie having NRA and
 b) lactic acid bacteria.

The invention relates to a composition comprising:
 a) bacteria belonging to the *Staphylococcus vitulinus* specie having NRA and
 b) lactic acid bacteria selected from the group consisting of bacteria of the *Lactococcus* genus, bacteria of the *Pediococcus* genus, and mixtures thereof.

The term "comprises" or "comprising" as used herein is intended to mean that a given composition comprises at least the components listed thereafter. Such a composition can therefore also comprise other additional components.

By way of example, the composition may comprise:
 a) the *Staphylococcus vitulinus* strain deposited under number CNCM I-3751 and
 b) lactic acid bacteria selected from the group consisting of bacteria of the *Lactococcus* genus, bacteria of the *Pediococcus* genus, and mixtures thereof.

By way of example, the composition may comprise:
 a) bacteria belonging to the *Staphylococcus vitulinus* specie and
 b) bacteria belonging to the *Pediococcus acidilactici* specie.

By way of example, the composition may comprise:
 c) the *Staphylococcus vitulinus* strain deposited under number CNCM I-3751 and
 d) bacteria belonging to the *Pediococcus acidilactici* specie.

By way of example, the composition may comprise:
a) bacteria belonging to the *Staphylococcus vitulinus* specie and
b) the *Pediococcus acidilactici* strain deposited under number CNCM I-4098.

By way of example, the composition may comprise:
a) the *Staphylococcus vitulinus* strain deposited under number CNCM I-3751 and
b) the *Pediococcus acidilactici* strain deposited under number CNCM I-4098.

The bacteria can be in any industrial stabilization form as previously described.

The invention also relates to a composition comprising:
a) bacteria belonging to the *Staphylococcus vitulinus* specie having NRA and
b) a medium that has been in contact with lactic acid bacteria and that is substantially free of bacteria.

By way of example, the composition may comprise:
a) bacteria belonging to the *Staphylococcus vitulinus* specie and
b) a medium which has been in contact with bacteria selected from the group consisting of bacteria of the *Pediococcus* genus, bacteria of the *Lactococcus* genus, and mixtures thereof, and is substantially free of bacteria.

By way of example, the composition may comprise:
a) the *Staphylococcus vitulinus* strain deposited under number CNCM I-3751 and
b) a medium which has been in contact with bacteria selected from the group consisting of bacteria of the *Pediococcus* genus, bacteria of the *Lactococcus* genus, and mixtures thereof, and is substantially free of bacteria.

By way of example, the composition may comprise:
a) the *Staphylococcus vitulinus* strain deposited under number CNCM I-3751 and
b) a medium which has been in contact with bacteria belonging to the *Pediococcus acidilactici* specie, and is substantially free of bacteria.

By way of example, the composition may comprise:
a) bacteria belonging to the *Staphylococcus vitulinus* specie and
b) a medium which has been in contact with the *Pediococcus acidilactici* strain deposited under number CNCM I-4098, and is substantially free of bacteria.

By way of example, the composition may comprise:
a) the *Staphylococcus vitulinus* strain deposited under number CNCM I-3751 and
b) a medium which has been in contact with the *Pediococcus acidilactici* strain deposited under number CNCM I-4098, and is substantially free of bacteria.

Preferably the medium which has been in contact with the lactic acid bacteria is a liquid medium.

Another object of the invention relates to bacteria having NRA suitable for carrying out the method of the invention. Accordingly, one aspect of the invention relates to the *Staphylococcus vitulinus* strain deposited under number CNCM I-3751. Another aspect of the invention relates to the *Staphylococcus carnosus* strain deposited under number CNCM I-3844. Another aspect of the invention relates to the *Staphylococcus xylosus* strain deposited under the number CNCM I-3845.

Another object of the invention relates to the *Staphylococcus vitulinus* strain deposited under number CNCM I-3751 alone or in combination with the *Staphylococcus carnosus* strain deposited under number CNCM I-3844 and/or the *Staphylococcus xylosus* strain deposited under the number CNCM I-3845.

The invention also relates to a kit for carrying out the method of the invention. Said kit comprises a composition as described above and nitrates. These nitrates can be all kinds previously described.

The following examples serve to illustrate the present invention but are in no way limiting.

Example 1

Determination of the NRA of *Staphylococcus vitulinus* CNCM I-3751, *Staphylococcus carnosus* CNCM I-3844 and *Staphylococcus xylosus* CNCM I-3845.

Three strains of *Staphylococcus* were tested for their NRA: *Staphylococcus vitulinus* CNCM I-3751, *Staphylococcus carnosus* CNCM I-3844 and *Staphylococcus xylosus* CNCM I-3845 at various temperatures: 4° C., 11° C., 25° C. and 44° C.

Method:

The NRA of the *Staphylococcus* strains (in freeze-dried form) was measured according to test A, as previously described. The period t was 16 hours when T was 4° C. or 11° C. The period t was 1 hour and a half when T was 25° C. The period t was 30 minutes when T was 44° C.

Results:

TABLE 1

NRA of *Staphylococcus* strains at different temperatures in μg of $NO_3^-$ converted per minute and per $10^{11}$ cfu

| | *Staphylococcus vitulinus* CNCM I-3751 | *Staphylococcus carnosus* CNCM I-3844 | *Staphylococcus xylosus* CNCM I-3845 |
|---|---|---|---|
| 4° C. | 30 +/− 3 | 5 +/− 1 | 6 +/− 1 |
| 11° C. | 84 +/− 8 | 56 +/− 5 | 35 +/− 4 |
| 25° C. | 435 +/− 21 | 507 +/− 25 | 122 +/− 6 |
| 44° C. | 2058 +/− 100 | 2029 +/− 100 | 377 +/− 19 |

At 4° C., the NRA of all three *Staphylococcus* strains was greater than 4 μg of $NO_3^-$ converted per minute and per $10^{11}$ cfu.

The NRA of the *Staphylococcus vitulinus* strain CNCM I-3751 was even greater than 25 μg of $NO_3^-$ converted per minute and per $10^{11}$ cfu. This strain therefore possesses a very high NRA at low temperature.

At 11° C., the NRA of *Staphylococcus carnosus* CNCM I-3844 was greater than 50 μg of $NO_3^-$ converted per minute and per $10^{11}$ cfu. The NRA of *Staphylococcus vitulinus* CNCM I-3751 was also very high, greater than 70 μg of $NO_3^-$ converted per minute and per $10^{11}$ cfu.

These two strains exhibit a significant NRA at low temperature. Other conventional strains tested at low temperature did not exhibit such a NRA, therefore demonstrating that these strains exhibit exceptional properties at low temperature.

At 25° C., the NRA of *Staphylococcus xylosus* CNCM I-3845 was greater than 100 μg of $NO_3^-$ converted per minute and per $10^{11}$ cfu; that of *Staphylococcus vitulinus* CNCM I-3751 greater than 400 μg of $NO_3^-$ converted per minute and per $10^{11}$ cfu; and that of *Staphylococcus carnosus* CNCM I-3844 greater than 450 μg of $NO_3^-$ converted per minute and per $10^{11}$ cfu.

At 44° C., the NRA of *Staphylococcus xylosus* CNCM I-3845 was greater than 300 μg of $NO_3^-$ converted per minute and per $10^{11}$ cfu, and the other two strains exhibited nitrate reductase activity greater than 1700 µg of $NO_3^-$ converted per minute and per $10^{11}$ cfu.

Example 2

Demonstration of the increase of the NRA of *Staphylococcus vitulinus* CNCM I-3751 by lactic acid bacteria or liquid having been in contact with lactic acid bacteria.

Example 2a

Effect of Lactic Acid Bacteria Themselves

The *Staphylococcus vitulinus* strain deposited under number CNCM I-3751 was used in freeze-dried form, in an amount of 1.44 mg/ml ($10^9$ cfu/ml). As demonstrated previously, this bacterium exhibits significant NRA at low temperature.

The strain of lactic acid bacterium *Pediococcus acidilactici* deposited under number CNCM I-4098 was also used in freeze-dried form, in an amount of 1.7 mg/ml (6×$10^8$ cfu/ml). This bacterium has a low acidifying capacity at low temperature.

Various temperatures were tested: 4° C., 11° C., 25° C. and 44° C. The NRA of the mixture was measured according to the same method as described above (test A).

The increase in NRA due to the addition of the lactic acid bacteria strain *Pediococcus acidilactici* CNCM I-4098 is calculated in the following manner: [(NRA of the mixture (*Staphylococcus vitulinus*+*Pediococcus acidilactici*)−NRA of the *Staphylococcus vitulinus*)/NRA of the *Staphylococcus vitulinus*]×100

Table 2 presents the percentage increase in NRA observed at different temperatures.

TABLE 2

Increase in the NRA of *Staphylococcus vitulinus* CNCM I-3751 due to the addition of lactic acid bacteria *Pediococcus acidilactici* CNCM I-4098, expressed as a percentage

| Temperature | *Staphylococcus vitulinus* CNCM I-3751 + *Pediococcus acidilactici* CNCM I-4098 |
|---|---|
| 4° C. | 31 |
| 11° C. | 52 |
| 25° C. | 37 |
| 44° C. | 27 |

These tests demonstrate that the NRA of a *Staphylococcus vitulinus* strain can be increased significantly by the addition of a biomass of freeze-dried lactic acid bacteria *Pediococcus acidilactici*. The synergistic effect is observed and is significant at all temperatures tested. The results are also excellent at low temperature (very good at 4° C. and even better at 11° C.)

Example 2B

Effect of Lactic Acid Bacteria Supernatants

The *Staphylococcus vitulinus* CNCM I-3751 strain was tested at 11° C. for its NRA. As above, the amount of *Staphylococcus vitulinus* CNCM I-3751 tested was 1.44 mg/ml ($10^9$ cfu/ml).

Supernatants of various lactic acid bacteria strains were prepared as follows:

Step 1: Rehydration of the freeze-dried biomass 10 g of freeze-dried biomass of lactic acid bacteria were resuspended in 90 g of tryptone salt liquid medium comprising 0.9% by weight of NaCl and 1% by weight of tryptone casein. The rehydration was carried out at room temperature for 10 minutes, with shaking at 200 rpm.

Step 2: Centrifugation

The bacterial suspension was then centrifuged at 6500 rpm for 10 minutes and the supernatant recovered. The latter was centrifuged again for 10 minutes at 6500 rpm.

Step 3: Filtration

The new supernatant thus harvested was finally filtered through a sterile filter with a porosity of 0.22 µm.

The increase in the NRA of the CNCM I-3751 strain at 11° C. was calculated by adding a supernatant of various strains of lactic acid bacteria belonging to the *Pediococcus* and/or *Lactococcus* genus, in an amount of 16.8 µl/ml or 20 µl/ml.

The following strains of lactic acid bacteria were tested:
*Pediococcus acidilactici* CNCM I-4098 (16.8 µl/ml or 20 µl/ml);
another *Pediococcus acidilactici* (20 µl/ml);
a *Pediococcus pentosaceus* strain (20 µl/ml) and
a *Lactococcus lactis* strain (20 µl/ml)

The values obtained with the freeze-dried materials of lactic acid bacteria (Example 2a)) are also indicated for comparison.

TABLE 3

Increase in the NRA of *Staphylococcus vitulinus* CNCM I-3751 due to the addition of lactic acid bacteria supernatants, expressed as a percentage

| Lactic acid bacteria or supernatant | | NRA increase (%) |
|---|---|---|
| *Pediococcus acidilactici* CNCM I-4098: biomass (1.7 mg/ml) | | 52 |
| supernatant of *Pediococcus acidilactici* CNCM I-4098 | (16.8 µl/ml) | 55 |
|  | (20 µl/ml) | 62 |
| *P. acidilactici* (20 µl/ml) | | 74 |
| *P. pentosaceus* (20 µl/ml) | | 61 |
| *L. lactis* (20 µl/ml) | | 43 |

Table 3 shows that the supernatants of freeze-dried lactic acid bacteria *Pediococcus acidilactici* CNCM I-4098 are just as effective as the freeze-dried bacteria alone in terms of stimulating the nitrate reductase activity of the *Staphylococcus vitulinus* CNCM I-3751.

In addition, the NRA stimulation observed increases with the amount of lactic acid bacteria supernatant added.

The results also demonstrate that the addition of supernatants obtained from various types of lactic acid bacteria makes it possible to significantly stimulate the NRA of *Staphylococcus vitulinus*.

Example 3

Example of manufacture of a cooked ham using the composition according to the invention A cooked ham was prepared according to the following method:

Step 0=pre-step (pre-conversion of nitrates to nitrites):

A source of nitrates (represents 0.15% by weight of the brine) was mixed with water (at a temperature of 15° C. and which represents 11.85% of the brine), until a homogeneous mixture was obtained.

A mixture of lyophilized bacteria (*Pediococcus acidilactici* CNCM I-4098, which represents 0.1% by weight of the brine and *Staphylococcus vitulinus* CNCM I-3751 which represents 0.02% by weight of the brine) was added and the whole was mixed until a homogeneous mixture was obtained.

The mixture was left to stand overnight at 11° C.

Step 1: Preparation of the Meat

An amount of 12 kg of meat was provided. The fat and the connective tissues were removed.

Step 2: Grinding

The meat was then finely ground.

Step 3: Preparation of the Brine

A given amount of water (represents 65.08% of the brine) was weighed out and salt (represents 17.5% of the brine) was added. The whole was mixed until the salt had completely dissolved.

The solution obtained in step 0, containing the source of partially reduced nitrates and the bacteria, and also dextrose (represents 5% of the brine) and sodium tripolyphosphate (represents 0.3% of the brine), were added and the resulting mixture was mixed for 5 minutes at a temperature of 7.5° C.

Step 4: Injection

The brine was injected into the ground meat obtained in step 2.

Step 5: Churning (Kneading)

The whole was mixed for 4 hours at 8 rpm continuously (80% vacuum), at a temperature of 10° C.

Step 6: Molding and Shaping

Step 7: Cooking

The ham was cooked at a surrounding temperature of 78° C. until 72° C. was reached at the heart of the product.

The ham was then cooled by showering.

The ingredients and proportions thereof are recalled in the following table:

TABLE 4

Ingredients used for the manufacture of the cooked ham in % by weight

| Recipe (150 ppm KNO$_3$ in the finished product) | % in the finished product | % in the brine |
|---|---|---|
| Water | | 65.08 |
| Salt | 1.75 | 17.50 |
| Dextrose | 0.50 | 5.00 |
| Water (used in step 0 for the preactivation of the color) | | 11.85 |
| Sodium tripolyphosphate | 0.03 | 0.30 |
| *Pediococcus acidilactici* CNCM I-4098 | 0.01 | 0.1 |
| *Staphylococcus vitulinus* CNCM I-3751 | 0.002 | 0.02 |
| Nitrate (KNO$_3$) | 0.015 | 0.15 |
| | | 100.00 |

The ham rapidly developed an intense and stable red color.

The invention claimed is:

1. A composition comprising:
   a) bacteria belonging to the *Staphylococcus vitulinus* specie having nitrate reductase activity (NRA) and deposited with the Collection Nationale de Cultures de Microorganismes under the number CNCM I-3751, and
   b) lactic acid bacteria and/or a medium that has been in contact with lactic acid bacteria and that is substantially free of bacteria, wherein said lactic acid bacteria are selected from the group consisting of bacteria of the *Lactococcus* genus, bacteria of the *Pediococcus* genus and mixtures thereof, and wherein said NRA of the *Staphylococcus vitulinus* specie is greater than or equal to 50 µg of $NO_3^-$ converted per minute and per $10^{11}$ cfu, according to test A performed at 11° C. and/or wherein said NRA is greater than or equal to 4 µg of $NO_3^-$ converted per minute and per $10^{11}$ cfu according to test A performed at 4° C.

2. The composition according to claim 1 wherein the lactic acid bacteria are the *Pediococcus acidilactici* strain deposited under the number CNCM I-4098.

3. The composition according to claim 1, further comprising the *Staphylococcus xylosus* strain deposited under the number CNCM I-3845.

4. The composition according to claim 1, further comprising the *Staphylococcus carnosus* strain deposited under number CNCM I-3844.

5. The composition according to claim 1, wherein the lactic acid bacteria, or the medium in b) increases, at low temperature, the nitrate reductase activity (NRA) of the bacteria belonging to the *Staphylococcus vitulinus* specie in a), in the presence of nitrates, at a pH of between about 5.2 and 9.

6. The composition according to claim 5, wherein the low temperature is about 16° C. or lower.

7. The composition according to claim 1, wherein the bacteria belonging to the *Staphylococcus vitulinus* specie and the lactic acid bacteria and/or a medium that has been in contact with lactic acid bacteria and that is substantially free of bacteria are in a dried form.

8. The composition according to claim 1, wherein the bacteria belonging to the *Staphylococcus vitulinus* specie and the lactic acid bacteria and/or a medium that has been in contact with lactic acid bacteria and that is substantially free of bacteria are in a frozen form.

9. The composition according to claim 1, wherein the bacteria belonging to the *Staphylococcus vitulinus* specie and the lactic acid bacteria and/or a medium that has been in contact with lactic acid bacteria and that is substantially free of bacteria are in a freeze-dried form.

10. A kit for converting nitrates to nitrites comprising a composition according to claim 1 and nitrates.

11. A method for increasing the nitrate reductase activity (NRA) of bacteria belonging to the *Staphylococcus vitulinus* specie comprising the step of incubating said bacteria belonging to the *Staphylococcus vitulinus* specie in the presence of nitrates and lactic acid bacteria or a medium which has been in contact with lactic acid bacteria and is substantially free of bacteria at a pH comprised between 5.2 and 9, wherein said *Staphylococcus vitulinus* is deposited with the Collection Nationale de Cultures de Microomanismes under the number CNCM I-3751, and wherein said lactic acid bacteria are selected from the group consisting of bacteria of the *Lactococcus* genus, bacteria of the *Pediococcus* genus and mixtures thereof.

12. The method according to claim 11, wherein said medium is a liquid medium.

13. A method for converting nitrates to nitrites, comprising the step of contacting nitrates with by bacteria belonging to the *Staphylococcus vitulinus* specie having nitrate reductase activity (NRA), in the presence of:

lactic acid bacteria, at a pH comprised between 5.2 and 9 and/or a medium which has been in contact with lactic acid bacteria and is substantially free of bacteria, at a pH comprised between 5.2 and 9, wherein said *Staphylococcus vitulinus* is deposited with the Collection Nationale de Cultures de Microorganismes under the number CNCM I-3751, and wherein said lactic acid bacteria are selected from the group consisting of bacteria of the *Lactococcus* genus, bacteria of the *Pediococcus* genus and mixtures thereof.

14. The method according to claim 13 wherein said bacteria belonging to the *Staphylococcus vitulinus* specie having NRA possess NRA of greater than or equal to 50 μg of $NO_3^-$ converted per minute and per $10^{11}$ cfu according to a test A performed at 11° C.

15. The method according to claim 13 wherein said bacteria belonging to the *Staphylococcus vitulinus* specie having NRA possess NRA of greater than or equal to 5 μg of $NO_3^-$ converted per minute and per $10^{11}$ cfu according to a test A performed at 4° C.

16. The method according to claim 13 wherein the bacteria belonging to the *Staphylococcus vitulinus* specie are combined with the *Staphylococcus carnosus* strain deposited under the number CNCM I-3844, and/or the *Staphylococcus xylosus* strain deposited under the number CNCM I-3845.

17. The method according to claim 13, wherein said lactic acid bacteria is the *Pediococcus acidilactici* strain deposited under the number CNCM I-4098.

18. The method according to claim 13, wherein said nitrates are contained in a liquid preparation.

19. The method according to claim 13, wherein said nitrates are contained in a liquid buffer preparation.

* * * * *

UNITED STATES PATENT AND TRADEMARK OFFICE
CERTIFICATE OF CORRECTION

PATENT NO.       : 9,062,293 B2
APPLICATION NO.  : 13/139081
DATED            : June 23, 2015
INVENTOR(S)      : Lionel Gilet et al.

It is certified that error appears in the above-identified patent and that said Letters Patent is hereby corrected as shown below:

On the Title Page, in Item (73), under "ASSIGNEE," please correct the Assignee name to read:

--DUPONT NUTRITION BIOSCIENCES APS--

Signed and Sealed this
Twenty-ninth Day of March, 2016

Michelle K. Lee
*Director of the United States Patent and Trademark Office*